US006775852B1

(12) United States Patent
Alvarez et al.

(10) Patent No.: US 6,775,852 B1
(45) Date of Patent: Aug. 17, 2004

(54) URINE COLLECTING DEVICE

(76) Inventors: Daniel M Alvarez, 2306 Kapahu St., Honolulu, HI (US) 96813; Robert E Jenkins, 2609 Date St., #6, Honolulu, HI (US) 96826

( * ) Notice: Subject to any disclaimer, the term of this patent is extended or adjusted under 35 U.S.C. 154(b) by 0 days.

(21) Appl. No.: 10/436,436
(22) Filed: May 12, 2003
(51) Int. Cl.[7] ............................................... A47K 11/00
(52) U.S. Cl. ....................................................... 4/144.2
(58) Field of Search ............................... 4/144.1–144.4, 4/455, 452, 484, 301, 315; 600/580, 574, 573; 422/102, 59

(56) References Cited

U.S. PATENT DOCUMENTS

| | | | | |
|---|---|---|---|---|
| 3,811,136 A | * | 5/1974 | Whitney et al. | 600/573 |
| 3,832,738 A | * | 9/1974 | Kliemann | 4/144.1 |
| 4,569,090 A | * | 2/1986 | Muller | 4/144.2 |
| 5,457,823 A | * | 10/1995 | Mojena | 4/144.2 |
| 6,115,855 A | * | 9/2000 | Lorenzo | 4/484 |

* cited by examiner

Primary Examiner—Gregory L. Huson
Assistant Examiner—Huyen Le
(74) Attorney, Agent, or Firm—Michael I. Kroll

(57) ABSTRACT

A hands-free urine collecting device comprising a flexible sheet with an elastomeric element extending peripherally therearound wherein said flexible sheet is placed over a conventional toilet seat with said elastomeric member placed on the underside thereof to maintain the flexible sheet suspended above the toilet water. A recess in the flexible sheet provides access to a sample cup and is retained thereunder by looped elastic bands extending from the underside of said flexible sheet. An overflow recess is also provided to prevent excess urine from accumulating in the funnel formed by said flexible sheet.

8 Claims, 7 Drawing Sheets

URINE COLLECTING DEVICE

FIELD OF THE INVENTION

The present invention relates generally to urine collecting devices and, more specifically, to a new and improved urine specimen collecting device for collecting a urine specimen from men or women that can be used at home, hospitals or doctors office. The device resembles a shower cap having apertures, one aperture has an elastomeric band for engaging a toilet seat and another aperture has fastening means for attaching a specimen collecting cup thereunder and another aperture for overflow.

The shower cap shaped device is stretched over a toilet seat extending into the toilet forming a water proof funnel within the bowl of the toilet that drains into the specimen cup which is secured in its respective position at the vortex of the funnel by means of a plurality of elastomeric fasteners.

When the urine has been collected, the device is removed from the toilet seat and the collection cup is released from the elastomeric retaining straps and covered to prevent contamination.

DESCRIPTION OF THE PRIOR ART

There are other urine collecting devices designed for specimen collection. Typical of these is U.S. Pat. No. 1,127,151 issued to William Alford on Feb. 2, 1915.

Another patent was issued to Gerald La Gorce et al. on Aug. 6, 1957 as U.S. Pat. No. 2,801,426. Yet another U.S. Pat. No. 3,061,840 was issued to Goldie Presseisen on Nov. 6, 1962 and still yet another was issued on May 5, 1964 to Edward Hill as U.S. Pat. No. 3,131,403.

Another patent was issued to Frank Ott on Mar. 24, 1970 as U.S. Pat. No. 3,501,781. Yet another U.S. Pat. No. 3,540,433 was issued to Leonard Brockman on Nov. 17, 1970. Another was issued to Pearl Slover on May 1, 1984 as U.S. Pat. No. 4,445,235 and still yet another was issued on July 26, 1988 to Charlotte Booth-Cox as U.S. Pat. No. 4,759,086.

Another patent was issued to Mark Bressler et al. on Sep. 15, 1992 as U.S. Pat. 5,146,637. Yet another U.S. Pat. No. 6,151,972 was issued to Jacob Cloete Venter on Nov. 28, 2000. Another was issued to Stingley et al. on Apr. 10, 2001 as U.S. Pat. No. 6,212,698 and still yet another was issued on Mar. 19, 2002 to Webb et al. as U.S. Pat. No. 6,358,477.

U.S. Pat. No. 1,127,151

Inventor: William Dave Alford

Issued: Feb. 2, 1915

This invention relates to a sanitary closet and has for its principal object the production of a simple and efficient means for directing excreta and feces into a sack carried thereby, without danger of any of this refuse being lost, whereby the spreading of infectious diseases is prevented.

U.S. Pat. No. 2,801,426

Inventor: Gerald A. La Gorce et al.

Issued: Aug. 6, 1957

A disposable bag toilet, comprising: a seat-supporting rim and supporting means for said rim, a seat connected to the back of said rim by a hinge, a bag having two normally open top and having adjacent its upper edges draw string means having two string ends which close the bag when pulled in opposite directions, the upper edges of said bag being held between said rim and seat when the seat is down, the ends of said draw strings being fastened to said seat at a point spaced from said hinge and there being means on said rim guiding said draw string in movement in opposite directions as they are pulled in raising the seat, whereby the draw strings close said bag when the seat is raised.

U.S. Pat. No. 3,061,840

Inventor: Goldie Presseisen

Issued: Nov. 6, 1962

An inflatable bed pan comprising in combination, an inflatable member having a central cavity disposed therein, a disposable member having an outer flange adapted to rest on the upper surface of said inflatable member, a first closing string slidably arranged within the periphery of said outer flange, a lower compartment for excrement adapted to depend within said cavity, said lower compartment having an open upper end and a closed lower end, an inwardly extending lip integrally contoured at 30 said upper end, and a second closing string slidably arranged peripherally of said inwardly extending lip.

U.S. Pat. No. 3,131,403

Inventor: Edward J. Hill

Issued: May 5, 1964

In an adult urine specimen collector, in combination, an elongated generally elliptical deeper at one end than at the other including an outwardly extending lip around the top thereof terminating in end extensions to accommodate manual holding thereof at each end, a generally vertical spout extending downwardly from said bowl at the deep end thereof including a diagonally upwardly disposed horn thereon; and a urine specimen bag closed except for an aperture through one side near the top thereof removably hung on said horn in suspended depending relationship over said spout with said spout and said horn disposed in said bag through said aperture therein.

U.S. Pat. No. 3,501,781

Inventor: Frank J. Ott

Issued: Mar. 24, 1970

A specimen-collecting receptacle for use in association with a toilet bowl comprising a generally dish-shaped body of such size and shape as to effectively close the opening of the toilet bowl when in normal operative position thereon for receipt of the whole of a specimen discharged into the toilet bowl opening, bracket means extending oppositely outwardly from the said body and adapted to extend in supportive engagement with a horizontal top surface of the toilet bowl edge to support the receptacle in the toilet bowl opening, each of the said bracket means comprising a downwardly-extending part engaging a corresponding vertical inner edge of the toilet bowl to locate the receptacle in register therewith, the body when in said normal operative position having in the bottom portion thereof a downwardly-extending well like portion of substantially smaller horizontal cross-section than the remainder of the body, the well-like portion decreasing progressively in cross-section to be of substantially smaller cross-section at its bottom end than at its top end to permit accurate measure at the bottom end of small quantities of specimen, the portions of the body wall which extend between the body opening and the said well-like portion being steep-sided to provide for movement under gravity of a specimen entering the of the bottom of the well-like portion, and graduation indicia at least on the well wall portion to be visible to an operator looking downwards into the receptacle.

U.S. Pat. No. 3,540,433

Inventor: Leonard Brockman

Issued: Nov. 17, 1970

The present invention discloses a feces strainer for use in easily and simply collecting a stool specimen, and is characterized by its ability to pass liquid constituents while retaining semisolid and solid constituents in a substantially nonadhesive manner so as to-facilitate the removal of solid feces specimen constituents from the strainer. In a preferred form, the feces strainer comprises a shallow receiving bag having a strainer means at the bottom taking the form of netting material made of a substantially liquid-impervious plastic fiber material, thus facilitating the washing, sterilization, and quick drying thereof, and also the previously mentioned, nonadhesive functional characteristics thereof with respect to solid and semisolid feces specimen constituents. In a preferred form the netting material may be made of a double layer configuration having slightly offset and thus effectively size-reduced, complete through-apertures through the double layers thereof, thus producing the effect of a filtering material having very small apertures while being made of a relatively inexpensive, easily obtained double layer form of netting material with each layer having substantially larger apertures. The strainer is provided with means for mounting it easily and simply on any of several different forms of conventional feces-receiving chambers to facilitate the stool collecting use therefor.

U.S. Pat. No. 4,445,235

Inventor: Pearl Slover et al.

Issued: May 1, 1984

A stool specimen collector for collecting a medical patient's feces for laboratory examination and test, the collector having a substantially impervious receptacle with a pair of side straps having an adhesive surface portion for contact adhesion to the top surface of a conventional toilet seat, the container being suspend below the toilet seat and above the surface of the toilet water, position to catch and retain a fecal specimen.

U.S. Pat. No. 4,759,086

Inventor: Charlotte Booth-Cox

Issued: Jul. 26, 1988

A disposable receptacle for receiving bodily waste, comprising of a fluid permeable inner layer and in impermeable outer layer, with an absorbent outer layer, with an absorbent layer in between, and a rim portion with fastening means to attach the receptacle so it depends downwardly through the hole in a bed pan or toilet trainer.

U.S. Pat. No. 5,146,637

Inventor: Mark Bressler et al.

Issued: Sep. 15, 1992

A hands-free female and male urine collection apparatus has a body with connected side, front, rear and bottom wall, with the side and front walls inclined inwardly. Portions of the bottom wall are inclined downwardly from the front wall towards the back wall and opposed portions of the bottom wall are inclined downwardly and inwardly from the side walls. The bottom wall terminates in a funnel shaped drain having a depending outlet. An adapter depends from the bottom wall and includes a flange to slidably receive a flanged cup. A plurality of right angularly related mount strips or other mount device extends radially outward from the body and are adapted to supportably bear upon a toilet bowl.

U.S. Pat. No. 6,151,972

Inventor: Jacob Venter et al.

Issued: Nov. 28, 2000

A urine sampling device (1) which facilitates urine sampling of female and infirm patients which is adapted to be associated with a toilet bowl (2) to collect a sample while the patient passes urine while seated on the toilet, wherein the urine sampling device (1) comprising an elongated trough member having a width substantially greater than its depth to define a generally pan-like trough, the trough member being fitted at a first end thereof with an attachment formation (3) by means of which the device (1) may in use be mounted in the toilet bowl (2) so that the trough member extends at a suitable angle to the horizontal so as to intercept a stream of urine being passed by a patient seated on the bowl (2), and also so as to minimize splashing of such urine onto the patient, the device (1) further including a urine sample collecting arrangement (4, 5).

U.S. Pat. No. 6,212,698

Inventor: Beverly Stingley et al.

Issued: Apr. 10, 2001

A urine collection kit includes a flexible mounting strip positioned atop the toilet bowl rim for clamping thereto by the toilet seat. A plastic bag is attached to the mounting strip and depends into the toilet bowl upon strip clamping. Urine flow is directed towards a collection cup releasably seated within a port in the bottom of the bag. Adjacent the port are a plurality of slots and a second discharge port for passage of urine overflow therethrough to preclude urine back splash onto a seated patient. The second discharge port includes a tube depending below the cup to preclude urine flow thereon. The front portion of the bag includes additional slots allowing for a collapsed storage position.

U.S. Pat. No. 6,358,477

Inventor: Bellinda Webb

Issued: Mar. 19, 2002

A collection device (10, 50) for urine samples in which a support (14, 56) is received on a seat of a commode. The support includes a funnel (16, 52) that depends from a first edge of the support about a perimeter thereof and tapering inwardly defines an open distal end (18, 52) opposed to the first edge. A collection cup (24, 60) is removably attached to the distal end of the funnel. The collection cup, being disposed inwardly of a commode with the support received on a seat thereof, receives a urine specimen from a patient occupying the commode and the collection cup, being detached from the funnel, carries the sample for analysis while the remainder of the collection device is disposed of.

While these urine sample collectors may be suitable for the purposes for which they were designed, they would not be as suitable for the purposes of the present invention, as hereinafter described.

SUMMARY OF THE PRESENT INVENTION

A primary object of the present invention is to provide a urine specimen collecting device that the collecting of urine specimens from men or women can be used at home, hospitals or doctors office.

Another object of the present invention is to provide a urine specimen collecting device that an elastomeric shower cap shaped device is stretched over a toilet seat forming a funnel within the bowl of the toilet.

Yet another object of the present invention is to provide a urine specimen collecting device that the elastomeric device is stretched over a toilet seat and funnels within a toilet bowls interior.

Still yet another object of the present invention is to provide a urine specimen collecting device that the funnel portions lowest point provides elastomeric means for attaching a specimen collecting cup.

Another object of the present invention is to provide a urine specimen collecting device that a urine collecting cup is provided and is attached to the lower portion of the funnel by means of an elastomeric fastener.

Additional objects of the present invention will appear as the description proceeds.

The present invention overcomes the shortcomings of the prior art by proving a new and improved urine specimen collecting device for the collecting of urine specimen from men or women that can be used at home, hospitals or doctors office having an elastomeric member, resembling a shower cap for engaging a toilet seat with a pair of apertures with one aperture having fastening means for attachment of a specimen collecting cup.

The shower cap shaped device is stretched around a toilet seat forming a funnel within the bowl of the toilet that drains into the specimen cup which is secured in its respective position at the vortex of the funnel by means of a plurality of elastomeric fasteners.

The foregoing and other objects and advantages will appear from the description to follow. In the description reference is made to the accompanying drawing, which forms a part hereof, and in which is shown by way of illustration specific embodiment in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
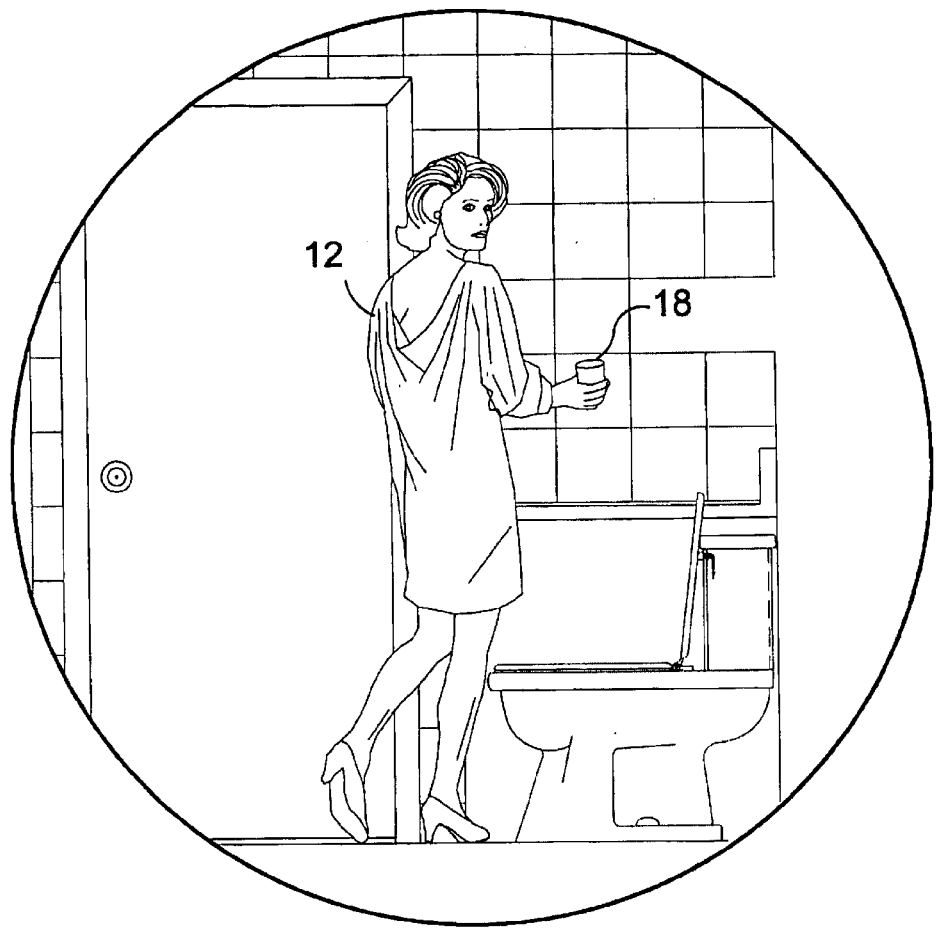
FIG. 1 is an illustrative view of prior art.

Turning now descriptively to the drawings, in which similar reference characters denote similar elements throughout the several views, the Figures illustrate the urine-collecting device of the present invention. With regard to the reference numerals used, the following numbering is used throughout the various drawing figures.

10 Urine-collecting device of the present invention
12 user
14 flexible sheet
16 peripheral edge of 14
18 top side of 14
20 underside of 14
22 elastomeric element of 16
24 elastic band of 16
26 container access aperture
28 container retaining means
30 first elastic band of 28
32 second elastic band of 28
34 overflow aperture
36 toilet seat
38 container
40 container cap

DETAILED DESCRIPTION OF THE PREFERRED EMBODIMENT

The following discussion describes in detail one embodiment of the invention. This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of prior art. The primary object of the present invention 10 is to provide an improved and convenient urine specimen collecting device 10 for the collecting of urine specimens from men and women that can be used at home, in hospitals or doctors office. The urine collecting devices prior to the present invention 10 may not be as easy to use, as disposable or cost effective. A woman 12 giving a urine sample may be confronted with shame and embarrassment, awkwardness, and an unsanitary situation, which would be the advantage of the present invention 10.

Figure 2:
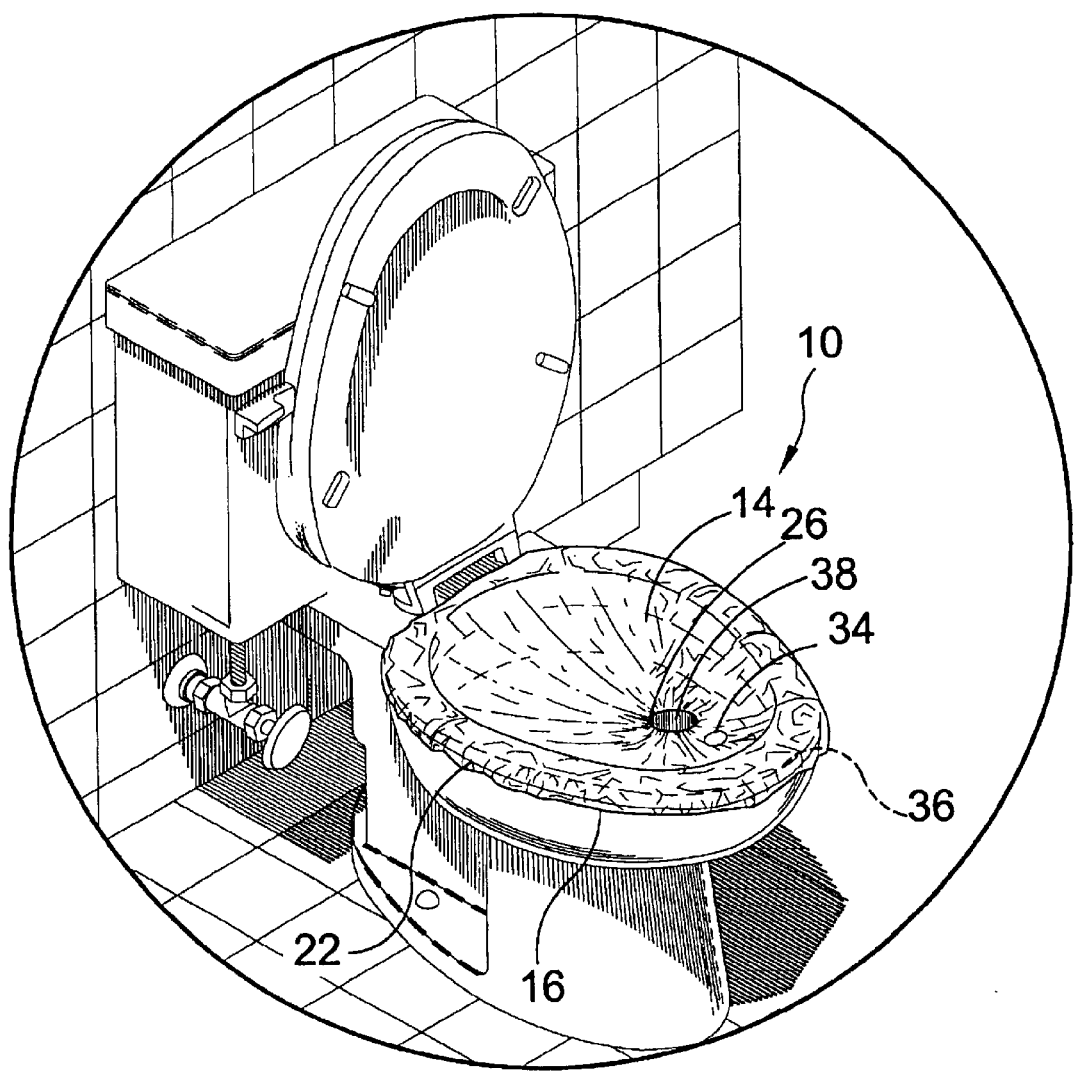
FIG. 2 is an illustrative view of the present invention in use.

FIG. 2 is an illustrative view of the present invention 10 in use. The present invention 10 is a urine collector comprised of a flexible sheet 14 having a peripheral edge 16 having an elastomeric element 22 for engaging a toilet seat 36 wherein said flexible sheet has a pair of aperture 26, 34 with one aperture 26 having fastening means thereunder for mounting a specimen collecting cup 38. The present invention 10 overcomes the shortcomings of prior art by providing a urine collector comprising a flexible sheet 14 having an elastomeric element 22 for engaging a toilet seat 36 with a pair of apertures wherein one aperture 34 is an overflow and the other 26 provides access to the specimen collecting cup 38.

Figure 3:
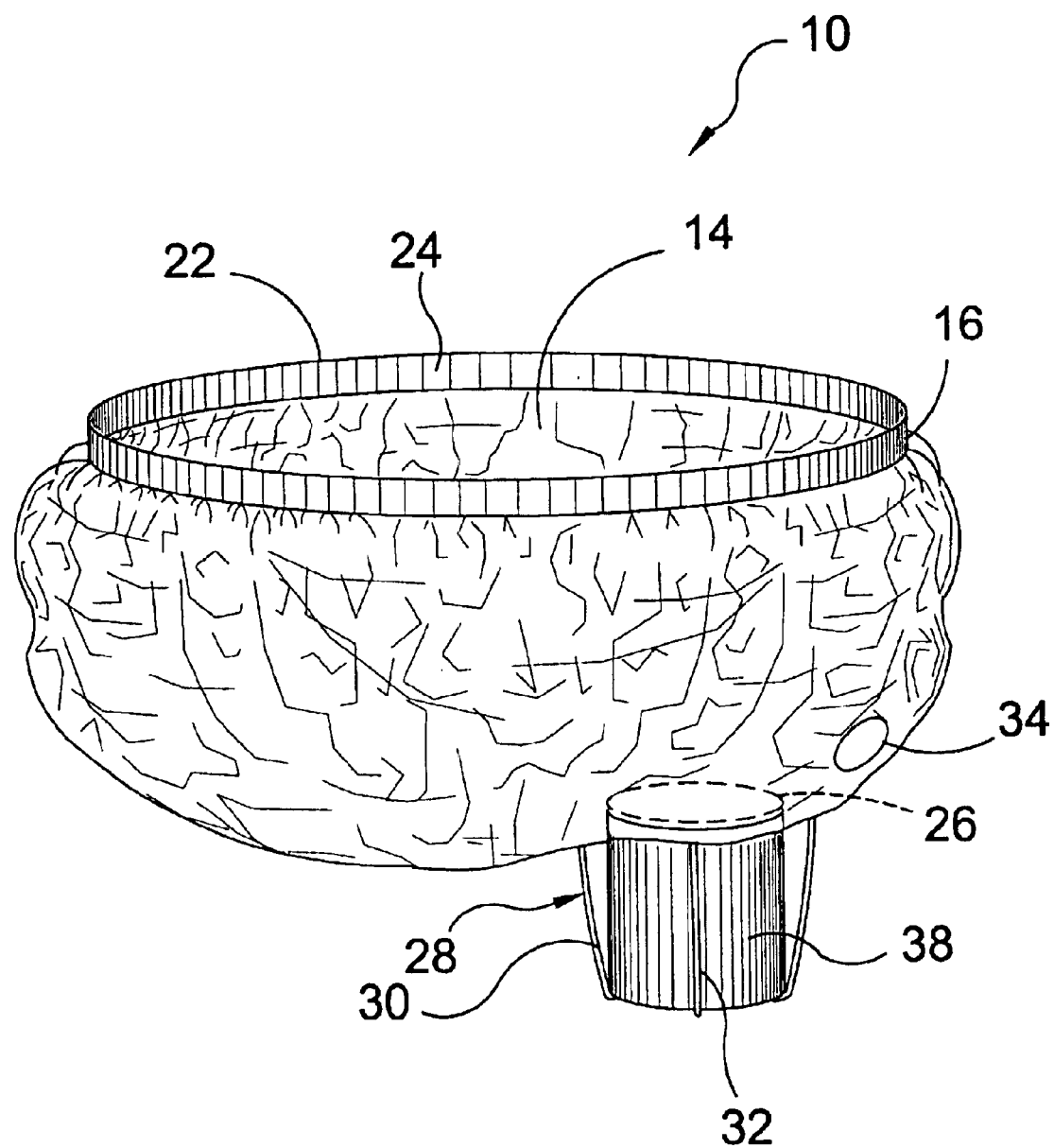
FIG. 3 is a perspective view of the present invention.

FIG. 3 is a perspective view of the present invention 10. Shown is a perspective view of the present invention 10 a urine collector device having an elastomeric element 22 for engaging a toilet seat 36 with a pair of apertures. Aperture 34 is an overflow aperture for excess urine and aperture 26 providing access to specimen collector cup 38 being retained under said container access aperture 26 by container retaining elements 30, 32.

Figure 4:
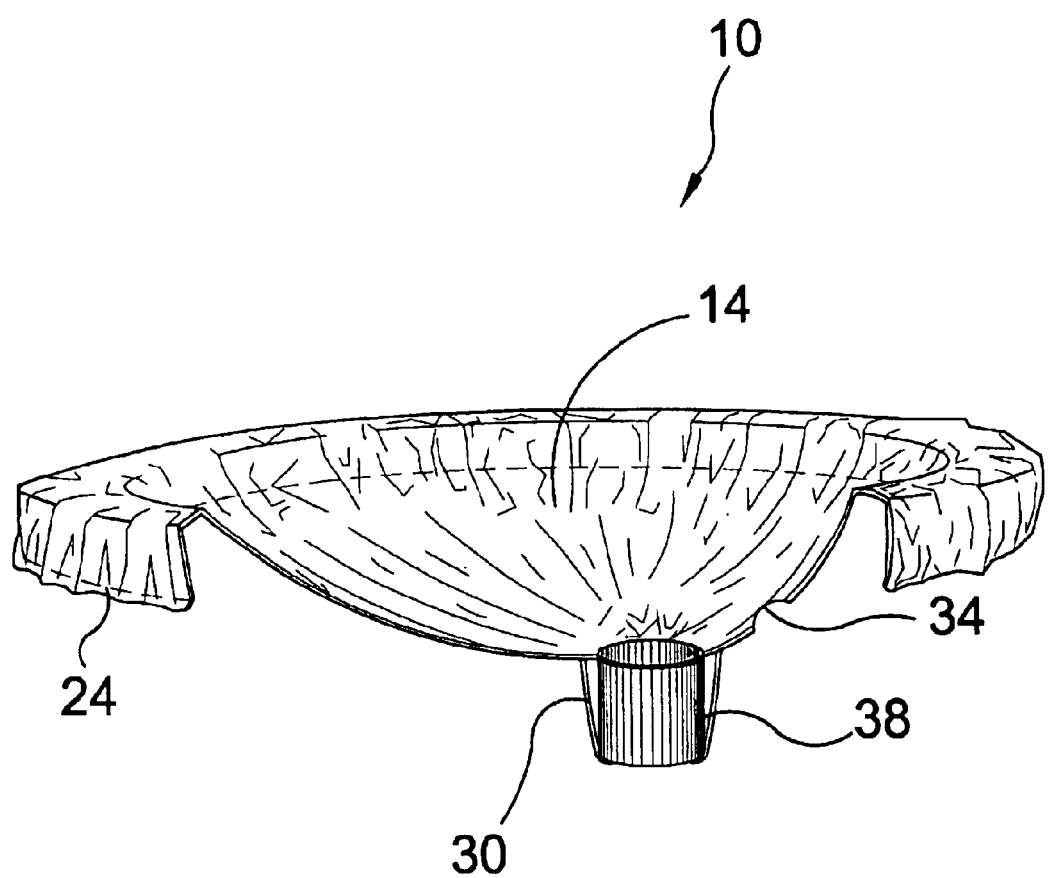
FIG. 4 is a cutaway view of the present invention.

FIG. 4 is a cutaway view of the present invention 10. Shown is a cutaway view of the present invention 10 as it would fold around a toilet seat 36 (not shown). The urine collector device of the present invention 10 having an elastomeric element 24 for engaging a toilet seat 36. A pair of apertures provide access to the specimen cup and specimen cup overflow aperture 34. Elastic band 30 is one of the fastening means for attachment of specimen cup 38.

Figure 5:
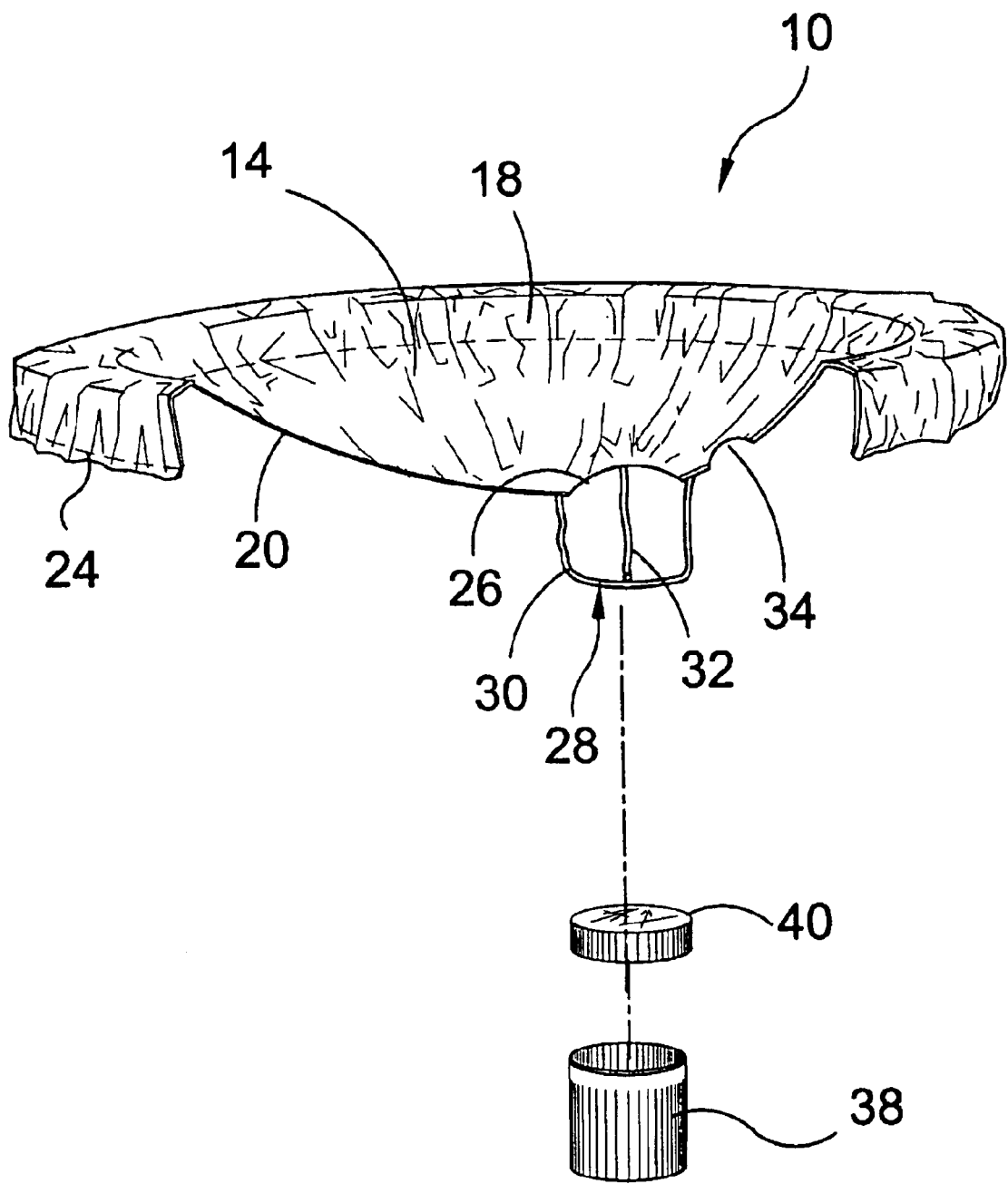
FIG. 5 is a cutaway view of the present invention.

FIG. 5 is a cutaway view of the present invention 10. Shown is a cutaway view of the present invention 10, as mounted to a toilet seat 36. The urine collector device of the present invention 10 having an elastomeric member 24 for engaging a toilet seat 36 with a pair of apertures 26, 34 and fastening means 28 comprised of elastic bands 30, 32 for attachment of a specimen collecting cup 38, shown removed.

Figure 6:
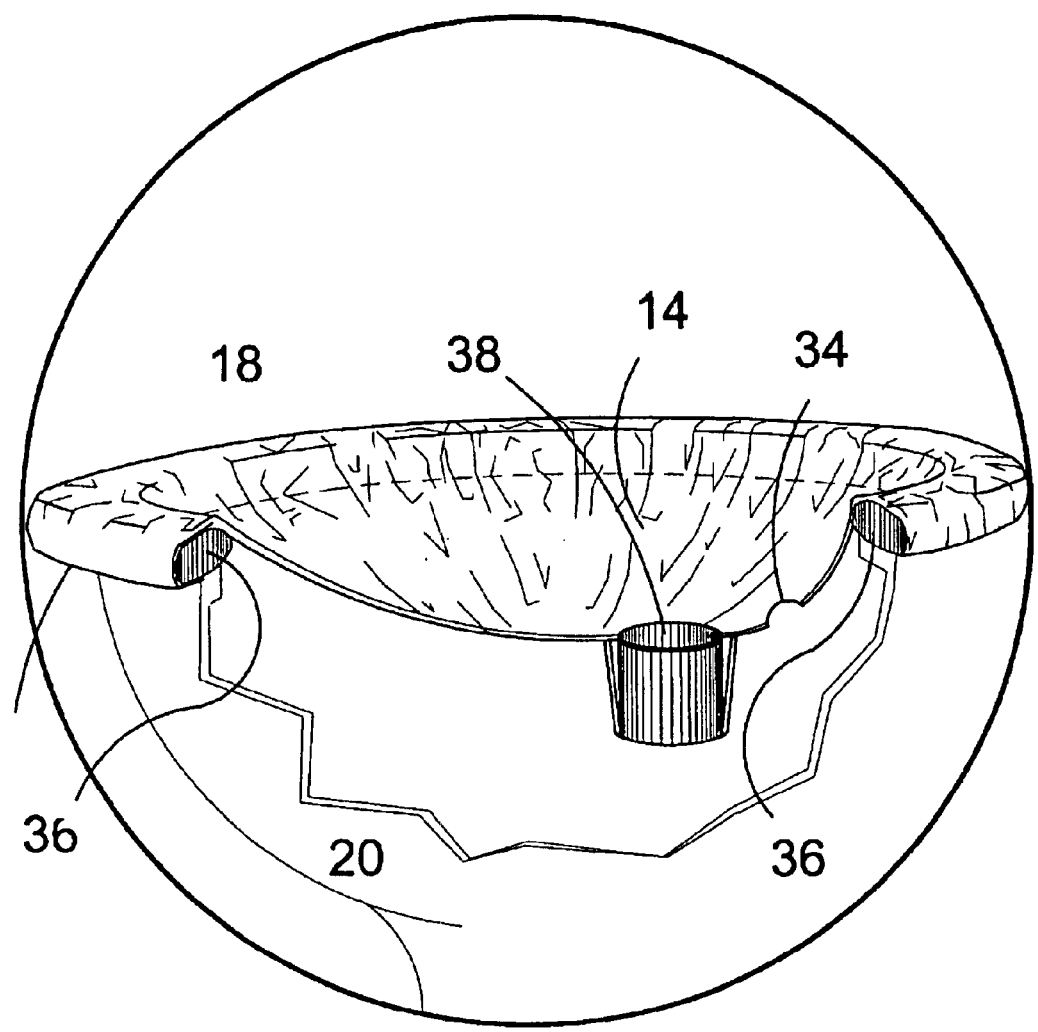
FIG. 6 is a detailed cutaway view of the present invention.

FIG. 6 is a detailed cutaway view of the present invention 10. Shown is a detailed cutaway view of the present invention 10, a urine collector device having an elastomeric member 24 for engaging a toilet seat 36 with a pair of apertures and fastening means for attachment of a specimen collecting cup 38.

Figure 7:
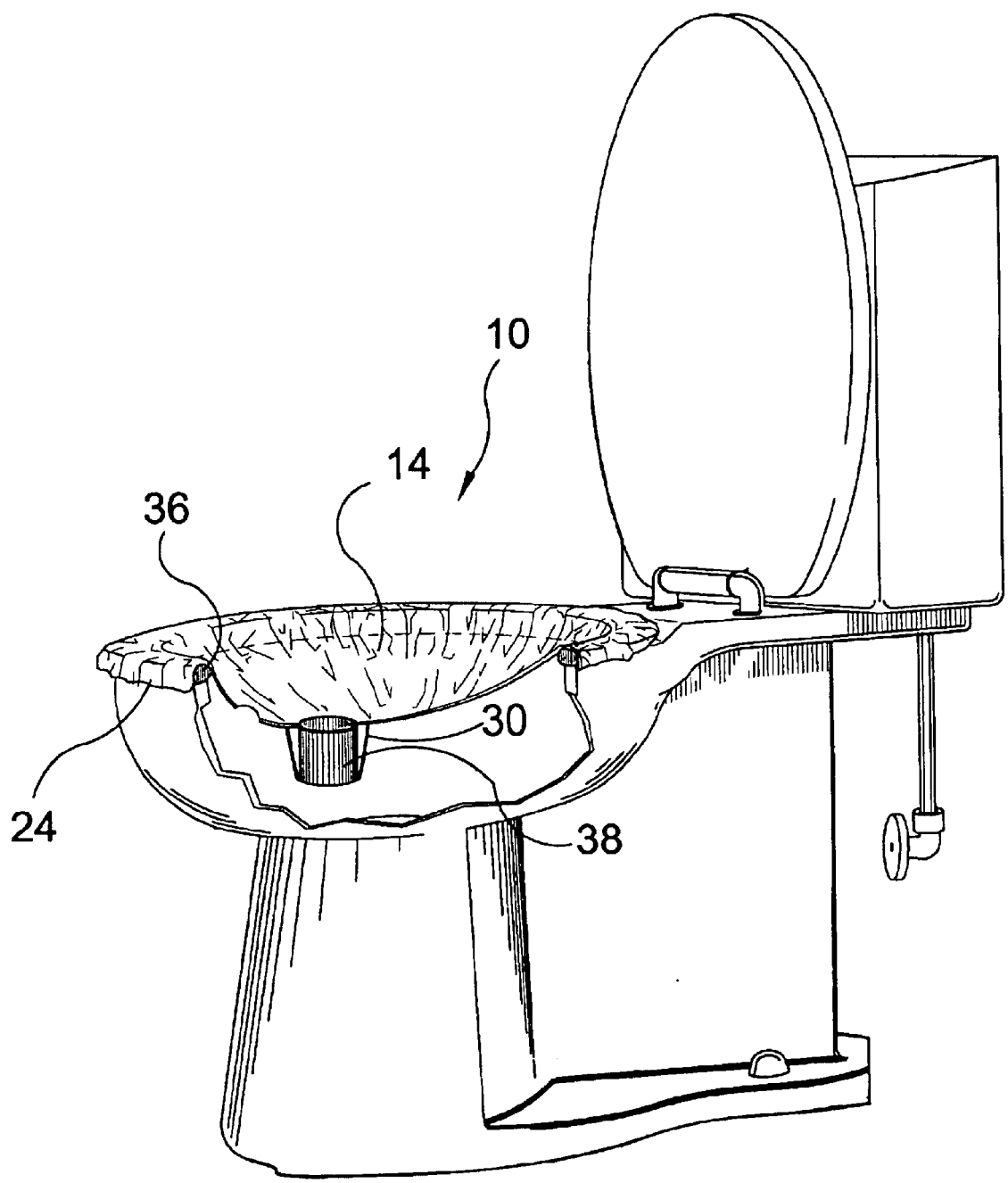
FIG. 7 is a cutaway perspective view of the present invention.

FIG. 7 is a cutaway perspective view of the present invention 10. Shown is a cutaway perspective view of the present invention 10, a urine collector device having an elastomeric member 24 for engaging a toilet seat 36 with a pair of apertures and fastening means for attachment of a specimen collecting cup 38.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claim is:

1. A hands-free urine-collecting device for suspending a container within a conventional toilet comprising:
   a) a flexible sheet having a top side, an underside and a peripheral edge;
   b) an elastomeric element disposed along and in communication with said peripheral edge of said flexible sheet in such a manner so as to allow said peripheral edge to expand or contact therewith;
   c) an aperture in said flexible sheet providing access to a container;
   d) means for retaining said container beneath said aperture; and
   e) said container retaining means comprises a first elastic band and a second elastic band, each band having a first end and a second end with said first end of said first elastic band disposed on said underside of said flexible sheet proximal to said access aperture and said second end on the opposing side thereof, said second elastic band is similarly positioned perpendicular to said first elastic band thereby forming a cradle underneath said container access aperture.

2. A hands-free urine-collecting device as recited in claim 1, wherein said elastomeric element is an elastic band having a first end and a second end; said first end and said second end having mating attachment means so that said second end loops back towards said first end thereby forming a loop that when in the static , contracted state has a circumference considerably less than that of said peripheral edge of said flexible sheet which takes on a crown-like configuration that is sized to be fitted over conventional toilet seats with said elastomeric element on the underside thereof and the central portion of said flexible sheet suspended over the seat and hanging slightly down over the bowl area.

3. A hands-free urine-collecting device as recited in claim 1, wherein said container access aperture is medially situated in an area of said flexible sheet towards the front of the toilet.

4. A hands-free urine-collecting device as recited in claim 1, further including a container configured to fit beneath said container access aperture.

5. A hands-free urine-collecting device as recited in claim 1, wherein tile weight of said container places the container access aperture at the nadir of said flexible sheet thereby urging any stray urine to flow along said flexible sheet and into said container.

6. A hands-free urine-collecting device as recited in claim 1, wherein said container further includes a securable cover for sealing the urine sample.

7. A hands-free urine-collecting device as recited in claim 1, further including an overflow aperture proximal to said container to allow for the egress of excessive urine into the toilet.

8. A hands-free urine-collecting device as recited in claim 1, wherein said flexible sheet is disposable.

\* \* \* \* \*